US00PP34609P3

(12) United States Plant Patent
Olesen

(10) Patent No.: US PP34,609 P3
(45) Date of Patent: Sep. 27, 2022

(54) MINIATURE ROSE PLANT NAMED 'POULPAR111'

(50) Latin Name: *Rosa hybrida*
Varietal Denomination: Poulpar111

(71) Applicant: Mogens Nyegaard Olesen, Fredensborg (DK)

(72) Inventor: Mogens Nyegaard Olesen, Fredensborg (DK)

(73) Assignee: Poulson Roser A/S, Fredensborg (DK)

( * ) Notice: Subject to any disclaimer, the term of this patent is extended or adjusted under 35 U.S.C. 154(b) by 25 days.

(21) Appl. No.: 17/300,625

(22) Filed: Sep. 7, 2021

(65) Prior Publication Data

US 2022/0095507 P1 Mar. 24, 2022

(30) Foreign Application Priority Data

Sep. 21, 2020 (QZ) ..... PBR 2020/2261

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121, 128
CPC ..... A01H 5/0222
See application file for complete search history.

(56) References Cited

PUBLICATIONS https://www.poulsenroser.dk/en/roses/ShowProduct/62679; Oct. 8, 2021; 2 pages.*

* cited by examiner

*Primary Examiner* — Kent L Bell

(57) ABSTRACT

A new garden rose plant of the Miniature class which has abundant, deep pink flowers and attractive foliage. This new and distinct variety has shown to be uniform and stable in the resulting generations from asexual propagation.

2 Drawing Sheets

Botanical designation: *Rosa hybrida.*

Variety denomination: 'Poulpar111'.

This application claims priority to Plant Breeder's Rights Application Number 2020/2261, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar111', originated as a single seedling from the stated cross.

The new variety may be distinguished from its male pollen parent and female seed parent primarily by the following characteristics. The male pollen parent plant has red flowers while the new variety has deep pink flowers. The female seed parent plant has near white flowers while the new variety has deep pink flowers. The objective of the hybridization of this rose variety was to create a new and distinct variety with unique qualities, such as:

1. Uniform and abundant deep pink flowers;
2. Vigorous, but compact growth when propagated on its own roots;
3. Exceptional disease resistance.

This combination of qualities is not present in previously available commercial cultivars of this type, known to the inventor, and distinguish 'Poulpar111' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar111' was selected in the spring of 2012 by the inventor as a single plant from the progeny of the aforementioned hybridization.

Asexual reproduction of 'Poulpar111' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpar111' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar111'.

Specifically illustrated in FIG. 1 of the drawings are open flowers viewed from above, and from the side, flower petals detached showing reproductive flower parts, sepals detached showing foliaceous appendages and flower receptacle.

Figure 1:
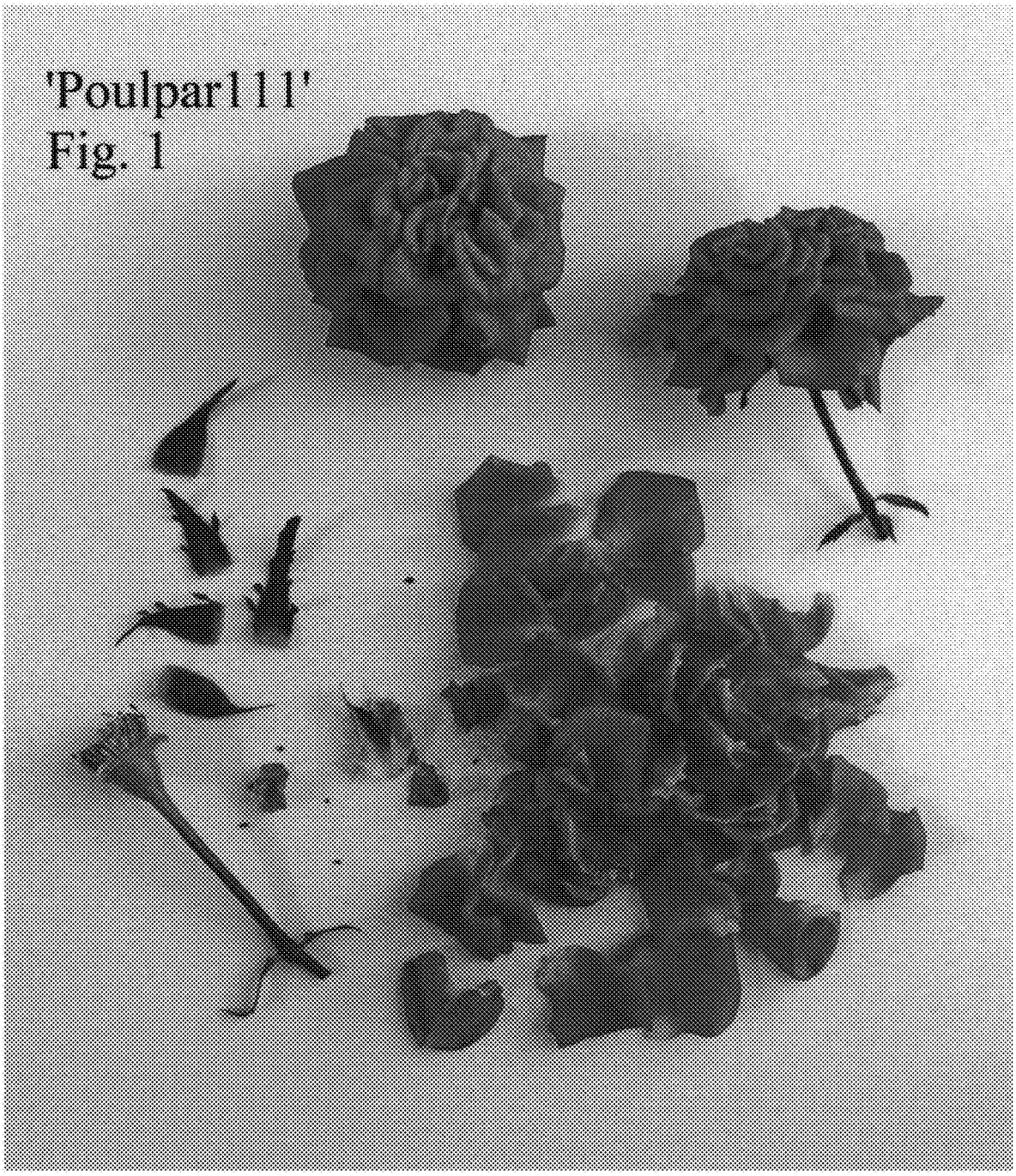
Figure 2:
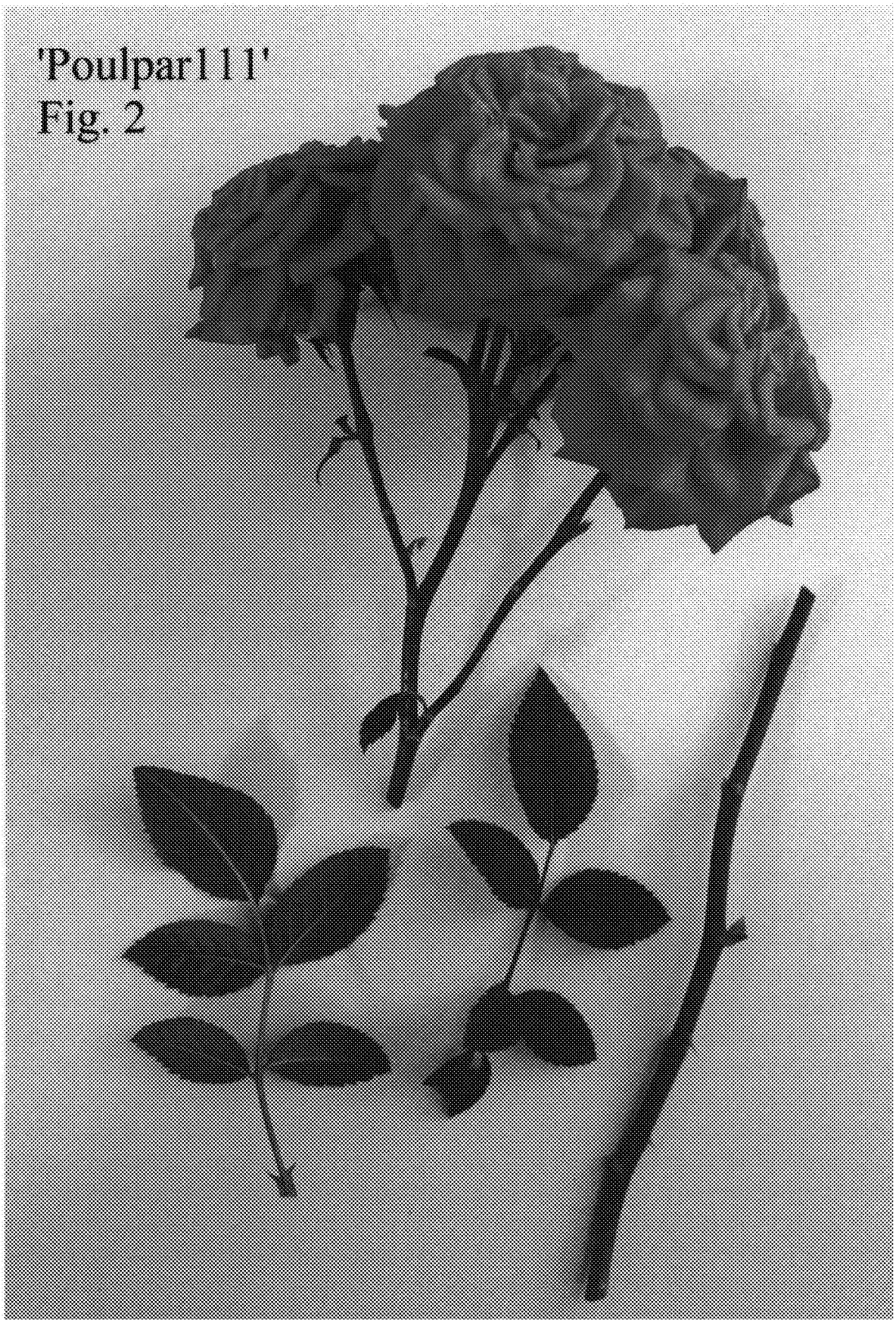

Specifically illustrated in FIG. 2 of the drawings are leaves, bare stem, and a cluster of open flowers on the branch.

Plants shown are 6 months of age.

DETAILED DESCRIPTION OF THE VARIETY

The following is a description of 'Poulpar111', as observed in its growth in a controlled environment greenhouse in Odense Denmark. Observed plants are 6 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpar097', U.S. Plant Pat. No. 29,120 are compared to 'Poulpar111' in Chart 1.

CHART 1

| | 'Poulpar111' | 'Poulpar097' |
|---|---|---|
| Petal Count | 56 | 45 |
| Flower Diameter | 47 | 65 |
| General Tonality of Flower Color | Red-Purple Group N57B | Red-Purple Group N57C |

FLOWER AND FLOWER BUD

Blooming habit: Continuous.

Flower bud:

*Size.*—Upon opening, 22 mm in length from base of receptacle to end of bud. Bud diameter is 14 mm.

*Bud form.*—Ovoid.

*Sepal inner surface.*—Color: Yellow-Green Group 147A & 147C. Surface: Lightly pubescent.

*Sepal outer surface.*—Color: Yellow-Green Group 144A. Texture: Smooth.

*Sepal shape.*—Generally: Subulate. Apex: Cirrhose. Base: Flat at union with receptacle.

*Sepal margin.*—Margins have strong foliaceous appendages on three of the five sepals.

*Sepal size.*—26 mm long, 9 mm wide.

*Receptacle.*—Texture: Smooth. Size: 7 mm in height, 10 mm wide. Color: Yellow-Green Group 144A. Shape: Funnel.

*Pedicel.*—Surface: Smooth. Length: 34 mm. Diameter: 2 mm on average. Color: Yellow-Green Group 144A. Strength: Strong.

*Peduncle.*—Length: 1 to 4 cm. Diameter: About 3 mm. Color: Yellow-Green Group 144A. Texture: Smooth.

Flower bud development: Flower buds are borne in clusters of 5 to 7 flower buds per stem.

Flower bloom:

*Fragrance.*—None.

*Duration.*—The blooms have a duration on the plant of approximately 21 days. Petals fall cleanly away from plant after flowers have fully matured.

*Size.*—Flower diameter is 47 mm when open. Flower depth is 23 mm.

*Flower shape.*—Very double rosette. After opening pompon flowers filled with masses of tiny petals.

*Shape of flower, side view.*—The upper portion is rounded. The lower portion is concave.

Petalage: Under normal conditions, flowers have about 56 petals.

General tonality of flower: Open flowers are Red-Purple Group N57B.

Petal color:

*Upper surface.*—Red-Purple Group N57B. At the basal zone White Group 157C.

*Lower surface.*—Red-Purple Group 58C, with streaks of Red-Purple Group 62D. At the basal zone White Group 157C.

Petals:

*Petal reflex.*—Strong.

*Margin.*—Entire and uniform. Moderate undulations.

*Shape.*—Broad and elliptic. Apex shape: Rounded. Base shape: Acute.

*Size.*—27 mm (l)×30 mm (w).

*Texture.*—Smooth.

*Thickness.*—Average.

Petaloids:

*Size.*—11 mm (l) by 9 mm (w).

*Quantity.*—About 12.

*Shape.*—Elliptical with an acute base and rounded apices.

*Color.*—On the upper surface Red-Purple Group N57B with a spot of White Group 157C at the point of attachment. The lower surface is Red-Purple Group 58C, with streaks of Red-Purple Group 62D. At the basal zone White Group 157C.

Reproductive flower parts:

*Pollen.*—None observed.

*Anthers.*—Size: 2 mm in length. Color: Greyed-Yellow Group 162B. Quantity: 35 on average.

*Filaments.*—Color: Greyed-Yellow Group 160D. Length: 4 mm.

*Pistils.*—Length: 4 mm. Quantity: 28 on average.

*Stigmas.*—Color: Greyed-Yellow Group 160B.

*Styles.*—Color: Green-White Group 157A.

*Location of stigmas.*—Inferior in location relative to the length of the filaments and the height of the anthers.

*Hips.*—None Observed.

PLANT

Plant growth: Upright, bushy. Plants are 30 to 38 cm in height, and 35 cm wide.

Stems:

*Color of juvenile growth.*—Yellow-Green Group 144B.

*Color of mature growth.*—Yellow-Green Group 144A.

*Length.*—Canes are about 15 to 19 cm from the base of the plant to the flowering portion.

*Diameter.*—About 4 mm.

*Internodes.*—On mature canes about 24 mm between nodes.

*Surface texture.*—Young wood: Smooth. Older wood: Smooth.

Long prickles:

*Incidence.*—About 2 prickles per 10 cm of stem.

*Size.*—Average length of prickles on mature stems is 8 mm.

*Shape.*—Upper portion is linear. Lower portion is concave.

*Color.*—Juvenile prickles: Greyed-Yellow Group 160C. Mature prickles: Greyed-Yellow Group 160C.

Plant foliage:

*Compound leaf.*—103 mm (l)×61 mm (w).

*Quantity.*—3 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 7 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 24 mm. Diameter: 2 mm. Upper surface color: Yellow-Green Group 144A. Lower surface color: Yellow-Green Group 144A.

*Rachis.*—Length: 35 mm. Diameter: 2 mm. Upper surface color: Yellow-Green Group 144A. Lower surface color: Yellow-Green Group 144A.

*Leaflet.*—Quantity: Normally 5 leaflets, occasionally 7. Margins: Serrated. Size: Terminal leaflets are about 42 mm long, 25 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The variety is susceptible to any insect pest normally associated with the species.

I claim:

1. A new and distinct variety of rose plant of the Miniature rose class named 'Poulpar111', substantially as illustrated and described herein, due to its abundant deep pink flowers, disease resistance, and extended period of bloom.

* * * * *

'Poulpar111'

'Poulpar111'